(12) United States Patent
Alavi

(10) Patent No.: US 9,394,431 B2
(45) Date of Patent: Jul. 19, 2016

(54) FORMALDEHYDE FREE BINDER COMPOSITIONS WITH UREA-ALDEHYDE REACTION PRODUCTS

(71) Applicant: JOHNS MANVILLE, Denver, CO (US)

(72) Inventor: Kiarash Alavi, Littleton, CO (US)

(73) Assignee: Johns Manville, Denver, CO (US)

( * ) Notice: Subject to any disclaimer, the term of this patent is extended or adjusted under 35 U.S.C. 154(b) by 0 days.

(21) Appl. No.: 14/684,629

(22) Filed: Apr. 13, 2015

(65) Prior Publication Data

US 2015/0232645 A1    Aug. 20, 2015

Related U.S. Application Data

(63) Continuation-in-part of application No. 14/334,731, filed on Jul. 18, 2014, which is a continuation-in-part of application No. 13/490,638, filed on Jun. 7, 2012, application No. 14/684,629, which is a continuation-in-part of application No. 13/675,414, filed on Nov. 13, 2012.

(51) Int. Cl.
| | | |
|---|---|---|
| *D01F 8/02* | (2006.01) | |
| *C08K 7/14* | (2006.01) | |
| *B05D 7/24* | (2006.01) | |
| *C07H 17/02* | (2006.01) | |

(52) U.S. Cl.
CPC ... *C08K 7/14* (2013.01); *B05D 7/24* (2013.01); *C07H 17/02* (2013.01); *B05D 2256/00* (2013.01); *B05D 2518/00* (2013.01)

(58) Field of Classification Search
None
See application file for complete search history.

(56) References Cited

U.S. PATENT DOCUMENTS

| | | | | |
|---|---|---|---|---|
| 6,207,278 | B1 * | 3/2001 | Jewell | D06M 13/123 428/364 |
| 2010/0189993 | A1 * | 7/2010 | Mori | C08J 7/047 428/317.5 |

* cited by examiner

*Primary Examiner* — Yun Qian

(74) *Attorney, Agent, or Firm* — Robert D. Touslee

(57) ABSTRACT

Fiber-containing composites are described that contain woven or non-woven fibers, and a cured binder formed from a binder composition that includes (1) a reducing sugar and (2) a crosslinking agent that includes a reaction product of a urea compound and a polycarbonyl compound. Exemplary reaction products for the crosslinking agent may include the reaction product of urea and an $\alpha,\beta$-bicarbonyl compound or an $\alpha,\gamma$-bicarbonyl compound. Exemplary fiber-containing composites may include fiberglass insulation.

5 Claims, 11 Drawing Sheets

FORMALDEHYDE FREE BINDER COMPOSITIONS WITH UREA-ALDEHYDE REACTION PRODUCTS

CROSS-REFERENCES TO RELATED APPLICATIONS

This application is a continuation-in-part of prior U.S. patent application Ser. No. 14/334,731, filed Jul. 18, 2014, entitled "Formaldehyde Free Binder Compositions With Urea-Aldehyde Reaction Products," which is a continuation-in-part of prior U.S. patent application Ser. No. 13/490,638, filed Jun. 7, 2012, entitled "Formaldehyde Free Binder Compositions With Urea-Aldehyde Reaction Products;" this application is also a continuation-in-part of prior U.S. patent application Ser. No. 13/675,414, filed Nov. 13, 2012, entitled "Viscosity Modified Formaldehyde-Free Binder Compositions." All three applications are incorporated herein by reference for all purposes.

BACKGROUND OF THE INVENTION

Organic binders for composite fiber products such as fiberglass insulation are moving away from traditional formaldehyde-based compositions. Formaldehyde is considered a probable human carcinogen, as well as an irritant and allergen, and its use is increasingly restricted in building products, textiles, upholstery, and other materials. In response, binder compositions have been developed that reduce or eliminate formaldehyde from the binder composition.

One type of these formaldehyde-free binder compositions rely on esterification reactions between carboxylic acid groups in polycarboxy polymers and hydroxyl groups in alcohols. Water is the main byproduct of these covalently crosslinked esters, which makes these binders more environmentally benign, as compared to traditional formaldehyde-based binders. However, these formaldehyde-free binder compositions also make extensive use of non-renewable, petroleum-based ingredients. Thus, there is a need for formaldehyde-free binder compositions that rely less on petroleum-based ingredient.

As an abundant and renewable material, carbohydrates have great potential to be an alternative to petroleum-based binders. Carbohydrates are already used as a component of some types for binders, such as Maillard binders that contain reaction products of reducing sugar carbohydrates and amine reactants. However, many types of carbohydrate-containing binders tend to become brittle when cured and form excessive particulates when the insulation is folded or compressed. Some carbohydrate-containing binders are also prone to accelerated degradation in humid environments and thus require additional conditioning and additives to improve their moisture/water resistance. Thus, there is a need to improve the stability and water resistance of carbohydrate-containing binder compositions to levels that are similar to or better than those of conventional, petroleum-based binder compositions. These and other issues are addressed in the present Application.

BRIEF SUMMARY OF THE INVENTION

Binder compostions are described that may include carbohydrates and a crosslinking agent made from the reaction product of a urea compound and an aldehyde-containing compound. Examples of the crosslinking agents include imidazolidine compounds made from the reaction product of urea (i.e., $H_2N$—$CO$—$NH_2$) and/or substituted ureas with diformaldehyde compounds such as glyoxal. A specific example of an imidazolidine crosslinking agent that may be used in the present binder compositions is 4,5-dihydroxyimidazolidin-2-one, which has the chemical structure:

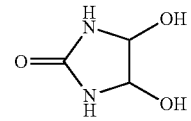

4,5-dihydroxyimidazolidin-2-one

The binder composition may be applied to a group of fibers to form a pre-cured amalgam of binder composition and fibers. The amalgam may then be exposed to curing conditions (e.g., heating) to facilitate the curing of the binder and formation of a fiber-containing composite. During the curing stage, the crosslinking agent crosslinks the reducing sugar to form a polymeric matrix that adheres the fibers together in the fiber-containing composite. Examples of these composites include fiber insulation (e.g., fiberglass insulation) for piping, ducts, buildings, and other construction applications.

Embodiments include binder compositions containing (1) a reducing sugar and (2) a reaction product of a urea compound and an aldehyde-containing compound. The binder composition may be applied to a group of fibers and exposed to curing conditions to form a fiber-containing composite of fibers bound by the cured binder.

A more specific embodiment of the binder composition may include dextrose as the reducing sugar, and 4,5-dihydroxyimidazolidin-2-one as the reaction product of a urea compound (in this case $H_2N$—$CO$—$NH_2$) and glyoxal (OHC—CHO). When the dextrose and 4,5-dihydroxyimidazolidin-2-one are exposed to binder curing conditions, the 4,5-dihydroxyimidazolidin-2-one crosslinks the dextrose (and polymerized forms of dextrose) to make the cured binder.

Embodiments further include fiber-containing composites containing woven or non-woven fibers and a cured binder formed from a binder composition that includes (1) reducing sugar and (2) a crosslinking agent that is a reaction product of a urea compound and an aldehyde-containing compound. The fibers may be one or more types of fibers chosen from glass fibers, mineral fibers, and organic polymer fibers (among others). Non-woven glass fibers may be included in composites for fiberglass insulation.

Embodiments still further include methods of binding fibers, where the methods include the step of applying a binder composition to a mat of woven or non-woven fibers, and then curing the binder composition applied to the fibers to make a fiber-containing composite. The binder composition may include a reducing sugar and a crosslinking agent formed as a reaction product between a urea compound and an aldehyde-containing compound, as described above.

Embodiments of the present technology may catalyze Maillard reactions in binder compositions without significant leaching of the catalyst and its derivatives from the finished product. The catalyst may include salts that are not water soluble, making the leaching of the salts from a finished product less likely. The catalyst salts may not form acids when exposed to water and may then reduce corrosion. In addition, the catalyst salts of the present technology may not be hygroscopic, and thus, unlike other salts, will not attract water, which may increase the likelihood of leaching. The catalyst salts also may reduce delamination between glass fibers and the binder composition, partly as a result of not forming acids that react with the glass fibers.

Embodiments of the present technology may include a carbohydrate binder composition. The carbohydrate binder composition may include a carbohydrate, a nitrogen-containing compound, and a catalyst. The catalyst may catalyze a reaction between the carbohydrate and the nitrogen-containing compound. The catalyst may include a salt of an oxyacid. The oxyacid may include a nonmetal atom, which may neither be hydrogen nor oxygen. The nonmetal atom may have a lower oxidation state than a maximum oxidation state of the nonmetal in a stable oxyacid.

Embodiments of the present technology may also include a method of reducing leaching from a fiber-containing composite. The method may include forming an aqueous dispersion of fibers. The method may also include applying a binder composition to the aqueous dispersion of fibers to form a binder-fiber mixture. The binder composition may include a carbohydrate, a nitrogen-containing compound, and a catalyst that catalyzes a reaction between the carbohydrate and the nitrogen-containing compound. The catalyst may include a salt of an oxyacid. The oxyacid may include a nonmetal atom that is neither hydrogen nor oxygen. The nonmetal atom may have a lower oxidation state than a maximum oxidation state of the nonmetal atom in a stable oxyacid. In addition, the method may include curing the binder-fiber mixture to form the fiber-containing composite. The fiber-containing composite may have a leach rate of ions less than a leach rate of ions from a fiber-containing composite formed by a method excluding the catalyst.

Embodiments may also include a fiber-containing composite. The fiber-containing composite may include glass fibers and a binder. The binder may include cured products from a carbohydrate binder composition. The carbohydrate binder composition may include a carbohydrate, a nitrogen-containing compound, and a catalyst that catalyzes a reaction between the carbohydrate and the nitrogen-containing compound. The catalyst may include a salt of an oxyacid. The oxyacid may include a nonmetal atom that is neither hydrogen nor oxygen. The nonmetal atom may have a lower oxidation state than a maximum oxidation state of the nonmetal atom in a stable oxyacid. The fiber-containing composite may have an ion leach rate less than an ion leach rate from a fiber-containing composite excluding the catalyst.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

Figure 1:
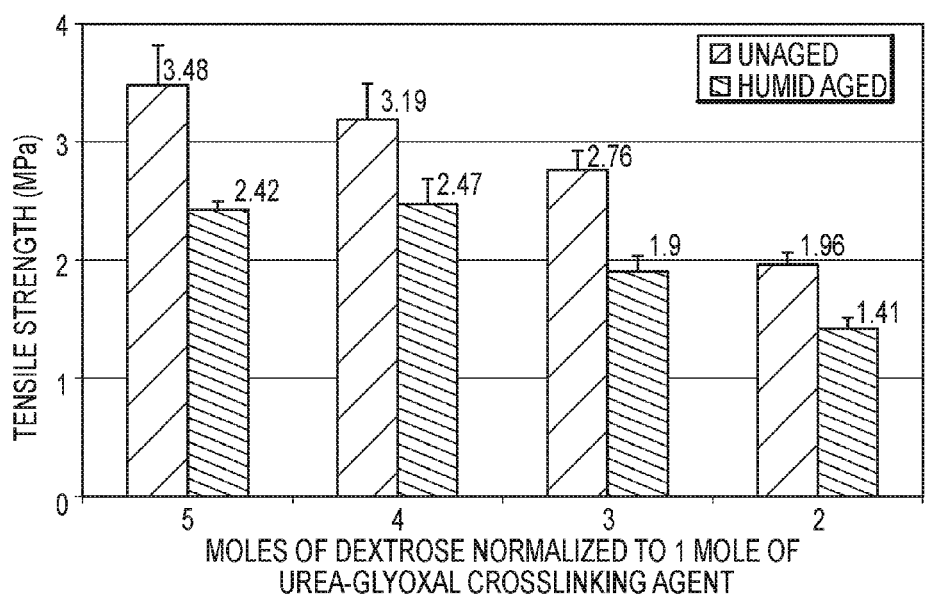
FIG. 1 shows a graph of dogbone tensile strength test results for different mole ratios of reducing sugar to crosslinking agent.

The present binders include renewable materials such as simple carbohydrates (e.g., dextrose, fructose) crosslinked by a reaction product of (i) a urea compound with (ii) an aldehyde and/or ketone containing compound. The urea compound may be a substituted our unsubstituted urea having the Formula (I):

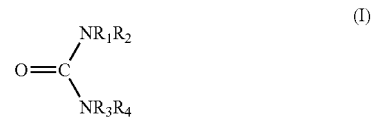

where $R_1$, $R_2$, $R_3$, and $R_4$ are independently chosen from a hydrogen moiety (H), an alkyl group, an aromatic group, an alcohol group, an aldehyde group, a ketone group, a carboxylic acid group, and an alkoxy group. Exemplary alkyl groups include straight-chained, branched, or cyclic hydrocarbons of varying size (e.g., $C_1$-$C_{12}$, $C_1$-$C_8$, $C_1$-$C_4$, etc.). Exemplary aromatic (i.e., aryl) groups include substituted or unsubstituted phenyl moieties, among other aromatic constituents. Exemplary alcohol groups include —ROH where R may be a substituted or unsubstituted, saturated or unsaturated, branched or unbranched, cyclic or acyclic, organic moiety. For example, R may be —(CH2)$_n$—, where n may be 1 to 12. Exemplary alcohols may also include polyols having two or more hydroxyl groups (—OH) in alcohol group. Exemplary aldehyde groups include —RC(=O)H, where R may be a monovalent functional group (e.g., a single bond), or a substituted or unsubstituted, saturated or unsaturated, branched or unbranched, cyclic or acyclic, organic moiety, such as —(CH2)$_n$—, where n may be 1 to 12. Exemplary ketone groups may include —RC(=O)R' where R and R' can be variety of carbon containing constituents. Exemplary carboxylic acid groups may include —R—COOH, where R may be a monovalent functional group, such as a single bond, or a variety of carbon-containing constituents. Exemplary alkoxy groups include —OR$_x$, where R$_x$ is an alkyl group.

The aldehyde and/or ketone containing compounds may include polyaldehydes (e.g., dialdehydes), polyketones (e.g., diketones), and compounds that have at least one aldehyde group and at least one ketone group. Examples include α,β-bicarbonyl compounds where carbonyl carbons are directly bonded as illustrated in the following Formula (II):

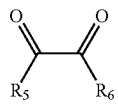

(II)

where $R_5$ and $R_6$ are independently chosen from a hydrogen moiety (H), an alkyl group, or an aromatic group. Exemplary α,β-carbonyl compounds include gloxyal, diacetyl, and benzil (i.e., 1,2-diphenylethane-1,2-dione).

Examples further include α,γ-bicarbonyl compounds where the carbonyl carbons are separated by one carbon atom as illustrated in the following Formula (III):

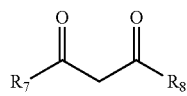

(III)

wherein $R_7$ and $R_8$ are independently chosen from a hydrogen moiety (H), an alkyl group, or an aromatic group. Exemplary α,γ-bicarbonyl compounds include malondialdehyde, and acetylacetone. In some instances, the $R_7$ and $R_8$ groups may independently also include alkoxide groups (—OR) where R represents an alkyl group, and amine groups (—NR'R''), where R' and R'' independently represent a hydrogen moiety (H) or an alkyl group. For example, the α,γ-bicarbonyl compounds may include malonic acid esters having Formula (IV):

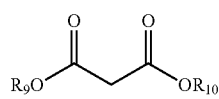

(IV)

where $R_9$ and $R_{10}$ are independently an alkyl group or an aromatic group.

Additional examples of α,γ-bicarbonyl compounds may include those with amide moieties such as those illustrated in Formula (V):

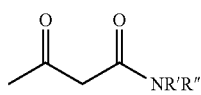

(V)

where R' and R'' are independently a hydrogen moiety (H) or an alkyl group.

Additional examples of α,γ-bicarbonyl compounds may further include those with alkoxy moieties such as those illustrated in Formula (VI):

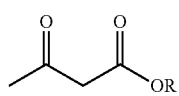

(VI)

where R represents an alkyl group.

Exemplary aldehyde and/or ketone containing compounds may include aldehyde-containing compounds having one or more (e.g., two or more) aldehyde functional groups. Examples of these aldehyde-containing compounds include acetaldehyde, propanaldehyde, butyraldehyde, acrolein, furfural, glyoxal, gluteraldehyde, and polyfurfural among others. Exemplary aldehyde-containing compounds may also include substituted glyoxal compounds having Formula (VII):

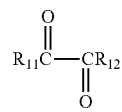

(VII)

where $R_{11}$ and $R_{12}$ may be independently hydrogen (H), an alkyl group, an aromatic group, an alcohol group, an aldehyde group, a ketone group, a carboxylic acid group, and an alkoxy group, among other groups.

The reaction products of the urea compound and the aldehyde and/or ketone containing compound depend on the types of compounds selected, as well as the mole ratio of each compound. For example, when the urea compound is urea and the aldehyde and/or ketone containing compound is glyoxal in a 1:1 mole ratio, the predominant reaction product is 4,5-dihydroxyimidazolidin-2-one represented by Formula (VIII):

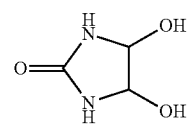

(VIII)

However, when excess urea increases the mole ratio of urea-to-glyoxal to 2:1, the predominant reaction product becomes a glycoluril compound shown in Formula (IX):

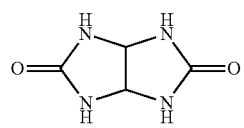

(IX)

Alternatively, when excess glyoxal shifts the mole ratio of urea-to-glyoxal to 1:2, the predominant reaction product becomes a (2R,3S,6R)-2,3,5,6-tetrahydroxy-1,4-diazabicyclo[2.2.1]heptan-7-one compound shown in Formula (X):

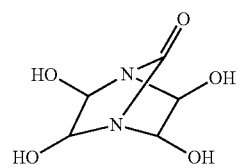

(X)

The reaction products of the urea compound and an aldehyde-containing compound having about a 1:1 mole ratio may include imidazolidine compounds of the Formula (XI):

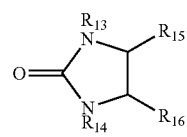

(XI)

where $R_{13}$, $R_{14}$, $R_{15}$, and $R_{16}$ are independently, —H, —OH, —NH$_2$, an alkyl group, an aromatic group, an alcohol group, an aldehyde group, a ketone group, a carboxylic acid group, and an alkoxy group. As noted above, when the reactants are urea and glyoxal, the reaction product may be 4,5-dihydroxyimidazolidin-2-one as shown in Formula (VIII).

Additional examples of reaction products of a urea compound with an aldehyde and/or ketone containing compound may include the reaction products of the above-described α,β-bicarbonyl compounds and α,γ-bicarbonyl compounds as represented by Formulas (XII)-(XVII) below:

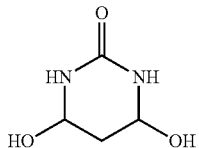
(XII)

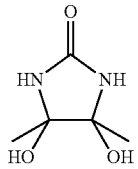
(XIII)

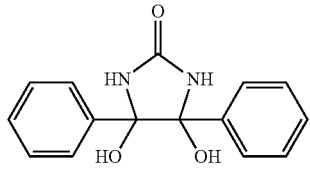
(XIV)

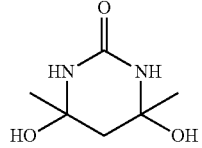
(XV)

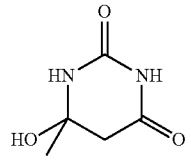
(XVI)

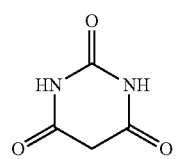
(XVII)

The reaction product of the urea compound and the aldehyde and/or ketone containing compound may act as a crosslinking agent for the reducing sugar. During a curing stage the crosslinking agent can bond to two or more reducing sugars (either polymerized or unpolymerized) to form a crosslinked, polymeric cured binder.

The reducing sugar may be any sugar having an aldehyde group, or ketone group that is capable of isomerizing to produce an aldehyde group. Exemplary reducing sugars include monosaccharaides such as glucoses (e.g., dextrose), fructose, glyceraldehyde, and galactose. They also include polysaccharaides such as lactose, maltose, xylose, and amylose, among others. The binder compositions may include a single reducing sugar or a combination of two or more reducing sugars as the reducing sugars in the composition.

The molar ratio of the (1) crosslinking reaction product of the urea compound and the and/or ketone containing compound to (2) the reducing sugar generally ranges from 1:2 to 1:50. Exemplary ratios of crosslinking agent to reducing sugar include a range from 1:4 to 1:10. FIG. 1 shows a graph of dogbone composite tests of tensile strength for binder compositions using a reaction product of urea [$CO(NH_2)_2$] and glyoxal [OCHCHO] as the crosslinking agent and dextrose [$C_6H_{12}O_6$] as the reducing sugar. The graph shows the tensile strength of the composites peaking at 4 to 5 moles of dextrose normalized for 1 mole of the crosslinking agent. This translates into a peak tensile strength at (crosslinking agent):(reducing sugar) mole ratios between 1:4 and 1:5. The tensile strength shows no significant increases for higher relative moles of the dextrose relative to the urea-glyoxal crosslinking agent. While not wishing to be bound by a particular theory, it is believed that the molar ratio between 1:4 and 1:10 facilitates the highest crosslinking density in the cured binder.

In addition to the reducing sugars, the present binder compositions may also include non-reducing sugars and celluloses, such as starches, modified starches, celluloses, modified celluloses, and dextrins (e.g., cyclodextrins and maltodextrins), among others. Embodiments also include binder compositions with any non-reducing sugars, as well as those that exclude one or more types of the above-described non-reducing sugars. For example, the binder composition may lack starch, modified starch, cellulose, modified cellulose, or dextrin (e.g., maltodextrin).

The binder composition may further include one or more additional components such as adhesion prompters, oxygen scavengers, solvents, emulsifiers, pigments, organic and/or inorganic fillers, flame retardants, anti-migration aids, coalescent aids, wetting agents, biocides, plasticizers, organosilanes, anti-foaming agents, colorants, waxes, suspending agents, anti-oxidants, and secondary crosslinkers, among other components. In some instances, some or all of the additional components are pre-mixed with the binder composition before it is applied to fibers and cured. In additional instances, some or all of the additional components may be introduced to the curable, curing, and/or cured fiber-containing composite during or after the initial binder composition is applied to the fibers.

The binder compositions may also include one or more catalysts to increase the rate of the crosslinking reactions between the reducing sugars and crosslinking agents when the composition is exposed to curing conditions. Exemplary catalysts may include alkaline catalysts and acidic catalysts. The acidic catalysts may include Lewis acids (including latent acids and metallic salts), as well as protic acids, among other types of acid catalysts. Lewis acid catalysts may a salt of a deprotonized anion such as a sulfate, sulfite, nitrate, nitrite, phosphate, halide, or oxyhalide anion in combination with one or more metallic cations such as aluminum, zinc, iron, copper, magnesium, tin, zirconium, and titanium. Exemplary Lewis acid catalysts include aluminum sulfate, ferric sulfate, aluminum chloride, ferric chloride, aluminum phosphate, ferric phosphate, and sodium hypophosphite (SHP), among others. Exemplary latent acids include acid salts such as ammonium sulfate, ammonium hydrogen sulfate, mono and dibasic ammonium phosphate, ammonium chloride, and ammonium nitrate, among other latent acid catalysts. Exemplary metallic salts may include organo-titanates and organo-zirconates (such as those commercially manufactured under the tradename Tyzor® by DuPont), organo-tin, and organo-aluminum salts, among other types of metallic salts. Exemplary protic acids include sulfuric acid, phosphoric acid, hydrochloric acid, nitric acid, sulfonic acid compounds (i.e, R—S(=O)$_2$—OH) such as p-toluenesulfonic acid and methanesulfonic acid, and carboxylic acids, among other protic acids. Catalyst compositions may also include combinations of two or more catalysts, for example the combination of ammonium sulfate and diammonium phosphate.

Catalyst Formulations with Reduced Leachable Salts

Various thermosetting binders have moved from including formaldehyde-based binders to binders that include polycarboxylic acids crosslinked with products of a Maillard reaction. Conventional, Maillard reaction catalysts may include sulfate, phosphate, nitrate, or carboxylate salts. These salts may be used in an amount from about 2.5% to 15% based on the mass of the solid resin. The catalyst salts may not be consumed during the curing process, and as a result may be present throughout the process and in the final product. These salts may leach out of the binder composition or the cured article. In particular, salts that contain sulfates or phosphate may react with water to form acids, such as sulfuric acid or phosphoric acid. These acids may lead to corrosion during the process or in the final product. These leached ions also may often be hygroscopic, which may increase water present, which may then increase the amount of leaching of the ions, and thus, may create a reinforcing feedback loop.

Additionally, the catalysts may affect glass that should be held together by the binder resins. The surface of glass fibers may include silicates, such as sodium, potassium, magnesium, aluminum, and boron silicates. Acids, such as sulfuric acid, may compete with the metal ions for the silicates. Acids may convert silicate to silica, affecting the properties of the glass surface. By reducing the metals and silicate concentrations on the glass surfaces, the glass surfaces are not as stable for binding with the resin. The catalysts may affect the interface between the resin and the glass and cause delamination.

Embodiments of the present technology may replace or reduce the amount of sulfates, phosphates, nitrates, or carboxylates in catalysts. Catalysts that replace the water soluble, hygroscopic ions with sulfonates, sulfamates, phosphonates, and other ions may decrease leaching from the resin and the final product without reducing cure kinetics, mechanical strength, and other properties of the resin or the final product.

Embodiments of the present technology may include a carbohydrate binder composition. The carbohydrate binder composition may include a carbohydrate, a nitrogen-containing compound, and a catalyst. The nitrogen-containing compound may be selected from the group consisting of an amino-amide, an amine salt of an organic acid, an ammonium salt of a carboxylic acid, and a reaction product of a urea compound and an aldehyde compound. Possible carbohydrates and nitrogen-containing compounds are discussed later. Embodiments may include or exclude any carbohydrate, nitrogen-containing compound, group of carbohydrates, or group of nitrogen-containing compounds described herein. The binder composition may be substantially or completely free of formaldehyde.

The catalyst may catalyze a reaction between the carbohydrate and the nitrogen-containing compound. The catalyst may include a salt of an oxyacid. The salt may be present in a concentration from about 2.5% to about 15%, from about 2.5% to about 10%, or from about 5% to about 10% on a solids basis of the carbohydrate binder composition in embodiments. The salt may include a reaction product of an oxyacid with a compound selected from the group consisting of an ammonia, an alkyl amine, an aryl amine, an alkanol amine, a diamine, and a polyamine. The alkyl amine may include methyl amine, ethyl amine, dimethyl amine, or trimethyl amine. The alkyl amine may include an alkyl group with 5 to 10 carbon atoms. The alkanol amine may include monoethanol amine, diethanol amine, or triethanol amine. The alkanol amine may include an alkanol group with 5 to 10 carbon atoms. The salt may include a metal ion. A salt with a metal ion may not lower the pH of the binder composition as much as other salts. The pH may be between about 5 and about 6. The metal ion may include an alkali metal ion, an alkaline earth metal ion, or a transition metal ion. The metal ion may include a lithium ion, a sodium ion, a potassium ion, a magnesium ion, a calcium ion, an iron ion, a zinc ion, a tin ion, or an aluminum ion.

The acid catalyst may include aluminum sulfonate, aluminum sulfamate, ferric sulfonate, ferric sulfamate, aluminum phosphonate, ferric phosphonate, ammonium sulfonate, ammonium sulfamate, ammonium hydrogen sulfonate, ammonium hydrogen sulfamate, mono and dibasic ammonium phosphonate, among other salts of an oxyacid. The catalyst may exclude any reaction products, metal ions, or groups of reaction products or metal ions described herein.

The oxyacid may include an ion selected from the group consisting of a sulfonate, a sulfamate, and a phosphonate. The oxyacid may include a nonmetal atom, which may be neither hydrogen nor oxygen. The nonmetal atom may be selected from the group consisting of nitrogen, sulfur, and phosphorous.

Exemplary catalysts may further include sulfamate-containing compounds, sulfonate-containing compounds, phosphonate-containing compounds, and phosphamate-containing compounds. For example, ammonium sulfamate ($[NH_4^+][SO_3NH_2^-]$) may be a catalyst used in the present binder compositions.

The nonmetal atom may have a lower oxidation state than a maximum oxidation state of the nonmetal in a stable oxyacid. For example, if the nonmetal atom is a nitrogen atom, the nitrogen may have an oxidation state of 4 or less. In a nitrate, nitrogen has an oxidation state of 5. If the nonmetal atom is a sulfur atom, the sulfur may have an oxidation state of 5 or less. In a sulfate, sulfur has an oxidation state of 6. If the nonmetal atom is phosphorous, the phosphorous may have an oxidation state of 4 or less. In a phosphate, phosphorous has an oxidation state of 5.

The oxyacid may be an alkyl sulfonic acid, an aryl sulfonic acid, a sulfamic acid, an alkyl phosphonic acid, an aryl phosphonic acid, a phosphorous acid, or a nitrous acid. The alkyl sulfonic acid may be a methyl sulfonic acid, an ethyl sulfonic acid, a propyl sulfonic acid, or a butyl sulfonic acid. The alkyl sulfonic acid may include an alkyl group including from 5 to 10 carbons. The aryl sulfonic acid may be a benzyl sulfonic acid, a p-toluene sulfonic acid, a sulfonated polystyrene, a sulfonated polystyrene-co-maleic anhydride, or a chloro sulfonated polyethylene. The sulfamic acid may be a methyl sulfamic acid, an ethyl sulfamic acid, a propyl sulfamic acid, a butyl sulfamic acid, a sulfamic acid including an alkyl group having 5 and 10 carbons, or derivatives thereof. The aryl phosphonic acid may be a methyl phosphonic acid, an ethyl phosphonic acid, a propyl phosphonic acid, or a butyl phosphonic acid. The alkyl phosphonic acid may include an alkyl group including from 5 to 10 carbons. The aryl phosphonic acid may include a p-toluene phosphonic acid or a phosphonated polystyrene.

Exemplary concentrations of the catalyst (or combination of catalysts) in the binder composition may have a range from about 1 wt. % to about 20 wt. % of the composition. For example, the catalyst concentration may range from about 1%, 2%, 3%, 4%, 5%, 6%, 7%, etc., on the low end, and 10%, 11%, 12%, 13%, 14%, 15%, 16%, 17%, 18%, 19%, or 20 wt. % on the high end. Exemplary catalyst concentrations may include about 5 wt. %, about 7.5 wt. %, about 8 wt. %, about 9 wt. %, and about 10 wt. %, among other concentrations.

The carbohydrate binder composition may include more than one catalyst. In addition to an oxyacid catalyst that described above, the carbohydrate binder composition may include an additional catalyst or catalysts. The additional catalyst or catalysts may include a salt of an oxyacid, where the oxyacid is a stable oxyacid with a nonmetal atom at the maximum oxidation state. The nonmetal atom may be neither hydrogen nor oxygen. For example, the salt of the additional catalyst may include a sulfate, nitrate, or phosphate. The additional catalyst or catalysts may have a total weight no more than one-ninth of the weight of the oxyacid catalyst previously described on a dry basis. In other words, the additional catalyst or catalysts may be no more than 10 wt. % of the total catalyst amount. In these and other embodiments, the additional catalyst or catalysts may be no more than 7 wt. % or no more than 5 wt. % of the total catalyst amount. The total catalyst amount may be called the catalyst package. The total catalyst amount may be between about 5 wt. % to about 10 wt. % of the total resin mass on a solids basis.

Figure 2:
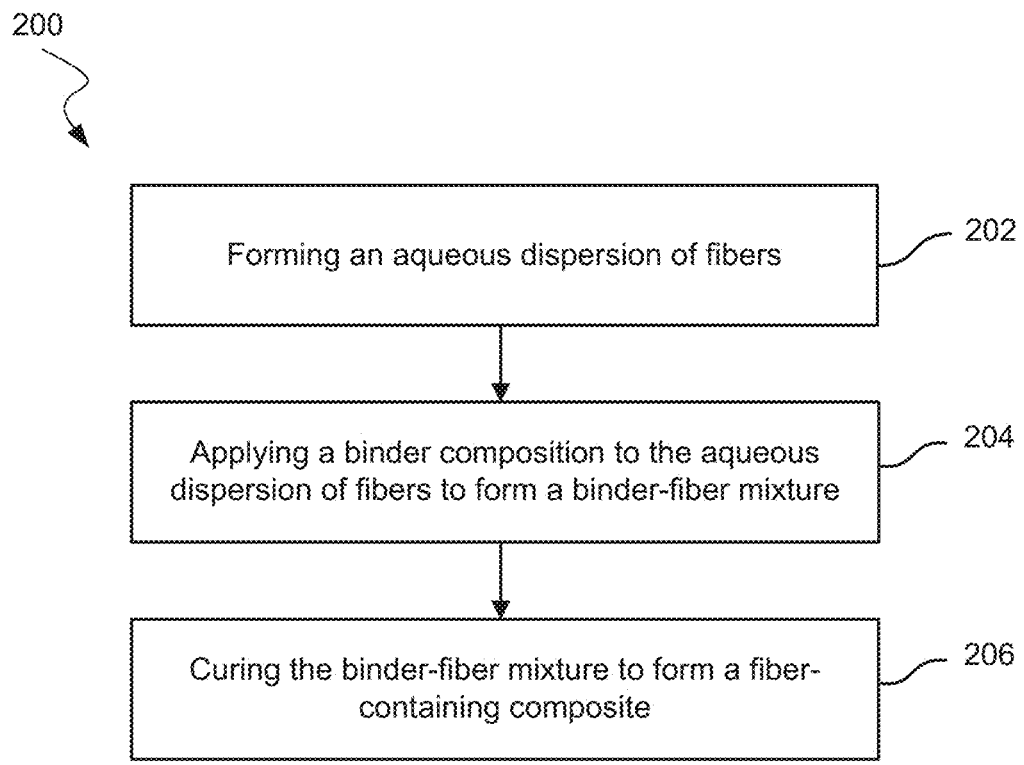
FIG. 2 shows a method of reducing leaching according to embodiments of the present technology.

Embodiments of the present technology may also include a method of reducing leaching from a non-woven glass fiber mat. FIG. 2 shows a method 200 of reducing leaching according to embodiments. Method 200 may include forming an aqueous dispersion of fibers 202. In some embodiments, method 200 may also include passing the dispersion through a mat forming screen to form a wet mat. Method 200 may further include applying a binder composition to the aqueous dispersion of fibers to form a binder-fiber mixture 204. Applying a binder composition may include applying a binder composition to a wet mat to form a binder-containing wet mat. Applying the binder composition to the wet mat may include curtain coating the binder composition on the wet mat.

The binder composition may include a carbohydrate, a nitrogen-containing compound, and a catalyst that catalyzes a reaction between the carbohydrate and the nitrogen-containing compound. The carbohydrate may include a reducing sugar. The reducing sugar may include dextrose, fructose, allose, galactose, xylose, ribose, maltose, cellobiose, or lactose. The nitrogen-containing compound may be include a diamine. The diamine may include ethylene diamine, 1,3-propanediamine, 1,4-butanediamine, 1,5-pentanediamine, 1,6-hexanediamine, α,α'-diaminoxylene, diethylenetriamine, triethylenetetramine, tetraethylenepentamine, and diamino benzene. The nitrogen-containing compound may include 4,5-dihydroxyimidazolidin-2-one. The nitrogen-containing compound may also include any compound described in this application.

The catalyst may include a salt of an oxyacid. The oxyacid may include a nonmetal atom that is neither hydrogen nor oxygen. The nonmetal atom may have a lower oxidation state than a maximum oxidation state of the nonmetal atom in a stable oxyacid. The catalyst may be any catalyst described in this application.

In addition, method 200 may include curing the binder-fiber mixture to form a fiber-containing composite 206. Curing may include curing the binder-containing wet mat to form the non-woven glass fiber mat. The fiber-containing composite may have a leach rate of ions less than a leach rate of ions from a fiber-containing composite formed by a method excluding the catalyst. The fiber-containing composite may be any fiber-containing composite described herein.

Embodiments may also include a fiber-containing composite. The fiber-containing composite may include glass fibers and a binder. The binder may include cured products from a carbohydrate binder composition. The carbohydrate binder composition may include a carbohydrate, a nitrogen-containing compound, and a catalyst that catalyzes a reaction between the carbohydrate and the nitrogen-containing compound. The catalyst may include any catalyst previously described. The fiber-containing composite may have an ion leach rate less than an ion leach rate from a fiber-containing composite excluding the catalyst.

Exemplary Binder Compositions and Fiber-Containing Composites

The pH of the present binder compositions may vary depending upon the types and relative concentrations of the components used. Typically the pH of the present binder compositions are slightly acidic to alkaline with a pH range of about 6 to 8 (e.g., 6.5 to 7.5). The binder compositions have a pH that creates relatively little or no acid-based corrosion of metal fabrication equipment.

The binder compositions may be used to make fiber-containing composites that include woven or non-woven fibers bound together by a cured matrix of the binder. The fibers in the composite may include one or more types of fibers chosen from glass fibers, carbon fibers, mineral fibers, and organic polymer fibers, among other kinds for fibers. At the conclusion of the curing stage, the cured binder may be present as a secure coating on the fiber mat at a concentration of approximately 0.5 to 50 percent by weight of the composition, for example the cured binder may be present at concentration of approximately 1 to 10 percent by weight of the composition.

The fiber-containing composites may take a variety of forms, for example construction materials including piping insulation, duct boards (e.g., air duct boards), and building insulation, reinforcement scrim, and roofing membranes, among other construction materials. Additional examples may include loose-fill blown insulation, duct liner, duct wrap, flexible duct media, pipe insulation, tank insulation, rigid plenum liner, textile duct liner insulation, equipment liner, oven insulation, elevated temperature board, elevated temperature wrap, elevated temperature panel, insulation batts and rolls, heavy density batt insulation, light density batt insulation, exterior foundation insulation board, and marine hull insulation, among other materials. The composites can also find use in printed circuit boards, battery separators, and filter stock, among other applications.

Figure 3A:
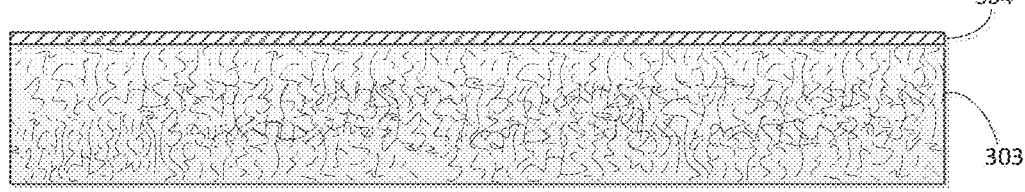
FIGS. 3A-C show simplified illustrations of exemplary composite materials according to embodiments of the invention.
Figure 3B:
Figure 3C:

FIG. 3A-C illustrate some of these exemplary composite materials. FIG. 3A is a simplified schematic of an exemplary fiber-containing batt material 302 that may be used for building insulation. The material 302 may include a batt 303 of non-woven fibers held together by the binder. The fibers may be glass fibers used to make fiberglass insulation (e.g, low-density or high-density fiberglass insulation), or a blend of two or more types of fibers, such as a blend of glass fibers and organic polymer fibers, among other types of fibers. In some examples, a facer 304 may be attached to one or more surfaces of the batt 303.

FIG. 3B is a simplified schematic of an exemplary fiber-containing composite board 306 that may be used as an insulation board, duct board, elevated temperature board, etc. The fibers in board 306 may include glass fibers, organic polymer fibers, carbon fibers, mineral fibers, metal fibers, among other types of fibers, and blends of two or more types of fibers.

FIG. 3C is a simplified schematic of an exemplary fiber-containing flexible insulation material 308 that may be used as a wrap and/or liner for ducts, pipes, tanks, equipment, etc. The fiber-containing flexible insulation material 308 may include a facer 310 attached to one or more surfaces of the fiber material 312. Exemplary materials for the facer 310 may include fire-resistant foil-scrim-kraft facing.

Specific examples of fiber-containing composites that use the present binder compositions include low-density fiberglass insulation (e.g., less than about 0.5 lbs/ft$^3$) and high-density fiberglass insulation.

The present binder compositions may be used in methods of binding fibers to make the fiber-containing composites. The fiber-containing composites may include fibers of one or more types, such as glass fibers, carbon fibers, and organic polymer fibers, among other types of fibers. The binder compositions used to make the composites may include a reducing sugar and a reaction product of a urea compound and an aldehyde-containing compound as described above. The methods may include the step of applying the binder composition to a mat of woven or non-woven fibers to make a curable binder-fiber amalgam. The curable amalgam is then cured to form the fiber-containing composite of fibers bound together by the cured binder.

The step of applying the binder composition to the fibers may be done by a variety of techniques including spraying, spin-curtain coating, curtain coating, and dipping-roll coating. The composition can be applied to freshly-formed fibers, or to fibers that have been cooled and processed (e.g., cut, coated, sized, etc.). The binder may be provided to the applicator as a premixed composition or may be supplied to the applicator in separate solutions for the crosslinking agent and the reducing sugar component. In some instances where the binder composition includes a solvent, a portion or all of the solvent may be removed from the composition before or after its application on the fibers.

The step of curing the binder composition may include exposing the composition applied to the fibers to an environment conducive to curing. For example, the curable amalgam of fibers and binder composition may be heated to a binder curing temperature. Exemplary binder curing temperatures may include a temperature range from 100° C. to 250° C. The curing amalgam may be heated to the curing temperature for a period of 1 minute to 100 minutes (e.g., 20 minutes).

The curing step may produce the finished fiber-containing composite, such as fiberglass insulation. In some exemplary methods, additional agents like an anti-dusting agent may be applied during or following the curing step.

Figure 4:
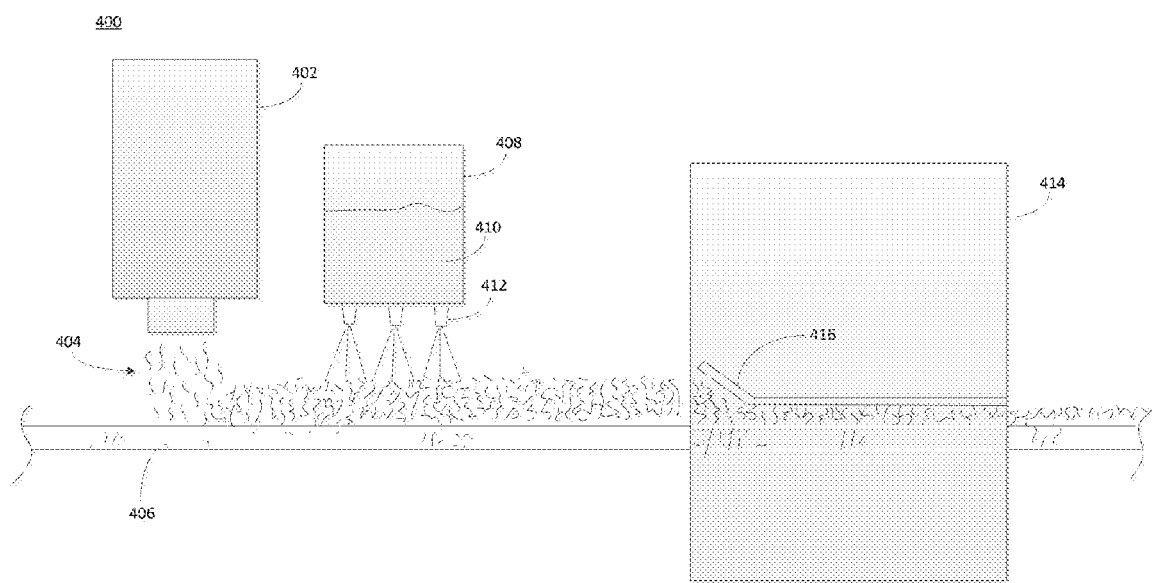
FIG. 4 depicts a simplified schematic of an exemplary fabrication system for making the fiber-containing composites according to embodiments of the invention.

FIG. 4 shows a simplified schematic of an exemplary fabrication system 400 for making the fiber-containing composites described above. The system 400 includes fiber supply unit 402 that supplies the fibers for the composite. The fiber supply unit 402 may be filled with pre-made fibers, or may include equipment for making the fibers from starting materials such as molten glass or organic polymers. The fiber supply unit 402 deposits the fibers 404 onto a porous conveyor belt 406 that transports the fibers under the binder supply unit 408.

The binder supply unit 408 contains a liquid uncured binder composition 410, that is deposited onto the fibers 404. In the embodiment shown, the binder composition 410 is spray coated onto the fibers 404 with spray nozzles 412, however, other application techniques (e.g., curtain coating, dip coating, etc.) may be used in addition to (or in lieu of) the spray coating technique illustrated by nozzles 412.

The binder composition 410 applied on fibers 404 forms a fiber and binder amalgam on the top surface of the conveyor belt 406. The belt 406 may be perforated and/or porous to allow excess binder composition 410 to pass through the belt 406 to a collection unit (not shown) below. The collection unit may include filters and circulation pumps to recycle at least a portion of the excess binder back to the binder supply unit 408.

The conveyor belt 406 transports the amalgam to an oven 414 where it is heated to a curing temperature and the binder composition starts to cure. The temperature of the oven 414 and the speed of the conveyor belt 406 can be adjusted to control the curing time and temperature of the amalgam. In some instances, process conditions may set to completely cure the amalgam into the fiber-containing composite. In additional instances, process conditions may be set to partially cure the amalgam into a B-staged composite.

The amalgam may also be compressed prior to or during the curing stage. System 400 shows an amalgam being compressed by passing under a plate 416 that tapers downward to decrease the vertical space available to the curing amalgam. The amalgam emerges from under the plate 416 in a compressed state and has less thickness than when it first made contact with the plate. The taper angle formed between the plate 416 and conveyor belt 406 can be adjusted to adjust the level of compression placed on the amalgam. The partially or fully cured composite that emerges from under plate 416 can be used for a variety of applications, including construction materials such as pipe, duct, and/or wall insulation, among other applications.

The present carbohydrate binder compositions may include one or more types of carbohydrate, nitrogen-containing compounds, and thickening agents, among other binder components. When the binder compositions are cured, the carbohydrates and nitrogen-containing compounds form a crosslinked polymer that in some instances is referred to as a Maillard polymerization product. Thickening agents are selected that create little or no interference with the crosslinking reaction of the polymer precursors so that the binder composition can be thoroughly and quickly cured after deposition on the fiber substrate (e.g., a glass fiber mat).

Exemplary thickening agents are added to control the viscosity of the binder compositions that are ultimately cured to make the adhesive binder component of the fiber product. The thickening agents may be polymeric materials and may be partially or fully water soluble. They are selected to enhance the binder compositions rheological properties (e.g., increase the composition's viscosity and surface tension) without substantially interfering with the composition's curability into an adhesive binder for the substrate fibers. Exemplary thickening agents may include polysaccharides, such as xanthan gum, guar gum, modified starches and the like; neutralized polyacrylic acid, such as sodium polyacrylate, modified celluloses, such as hydroxyethyl cellulose (HEC), carboxymethyl cellulose (CMC), as well as their soluble salts, polyacrylamides, and polyvinyl alcohols. The exemplary thickening agents may have a weight average molecular weight typically from 100,000 to 2,000,000 g/mol (e.g., 200,000 to 1,000,000 g/mol). The thickening agent (or agents) are typically added to the binder composition prior to its deposition on the fiber substrate, or alternatively may be added separately and approximately simultaneously with the other components of the binder composition to the fiber substrate.

The concentration of thickening agent in the binder composition may depend in part on the concentration of the other binder components in the composition. The carbohydrate binder compositions may be aqueous mixtures or solutions, and their viscosities depend in part on the how much the polymer precursors have been diluted by the water. For example, some concentrated binder compositions (e.g., solids concentrations of 45 to 70 wt. % or more) may have viscosities in the hundreds of centipoise at room temperature. The concentrated resins are typically diluted with water to, for example, a solids concentration of 10 to 30 wt. % solids (e.g., 10 to 20 wt. % solids), reducing the binder composition's viscosity to less than 3 cPs at room temperature. Other binder compositions may have functional viscosities at high concentrations (e.g., 20 cPs at 50 wt. % solids concentration) but should be diluted to address processing challenges such as LOI, weight, and uniformity problems for the applied binder composition.

Thickening agents may be added to increase the viscosity of the aqueous binder composition to a range of 7 to 50 cPs at room temperature (i.e., 20° C.), as measured by a Brookfield viscometer operating at a speed of 60 revolutions per minute. Typically, binder composition viscosities in this range can be achieved at thickening agent concentrations between 0.03 to 0.3 wt. % of the total composition. The concentration range of thickening agent can depend on the type of agent used. For example, adding hydroxyethyl cellulose to a concentration range of 0.05 to 0.3 wt. % may be sufficient to increase the composition's viscosity into a 7 to 50 cPs range. The same viscosity range may be met by adding 0.03 wt. % to 0.2 wt. % xanthan gum to the aqueous binder composition.

In addition to the thickening agents, the binder compositions may also contain a surfactant that provides more precise control over the surface tension of the composition. The surfactant may be added in amounts to achieve a surface tension for the binder composition of 35 to 50 mN/m (e.g., 38 to 48 mN/m, 40 to 47 mN/m, etc.). These surfactants may include cationic, anionic, and/or non-ionic surfactants.

The binder formulations of the binder compositions may include one or more types of carbohydrates and nitrogen-containing compounds. The nitrogen-containing compounds may act as crosslinking agents for the carbohydrates in the cured binder. The carbohydrates used in the binder formulations may include reducing sugars that contain at least one aldehyde group, or are capable of forming an aldehyde group through isomerization. Exemplary reducing sugars may include glucose (dextrose), fructose, glyceraldehyde, galactose, allose, xylose, ribose, maltose, cellobiose, and lactose, among others.

The nitrogen-containing compounds may include a variety of compounds that can distinguish the class of binder formulation. One class of binder formulations uses an amino-amide as the nitrogen containing compound, which itself is a reaction product of an amine with a saturated or unsaturated reactant. Another class of binder formulations has as the nitrogen-containing compound a reaction product of a urea compound and aldehyde-containing compound. Each of these classes of nitrogen-containing compounds are described more detail below.

1. Carbohydrate/Amino-Amide Binder Formulations

The nitrogen-containing compounds may include amines capable of undergoing conjugate addition with a saturated or unsaturated reactant to form an amino-amide. The amino-amide then reacts during curing with the carbohydrate to form a polyimide. The amino-amide addition products may be formed by mixing the amine and saturated or unsaturated reactant in an aqueous medium at room temperature. The resulting addition products are either water-soluble, water-dispersible, or are present as an emulsion. In some binder formulations, the formation of the amino-amide from the reaction of the amine precursor with the saturated or unsaturated reactant may occur before the introduction of the carbohydrate, while other formulations mix all three precursors (i.e., the amine, saturated or unsaturated reactant, and carbohydrate) before the amino-amide is formed.

Each amine may have two or more primary and/or secondary amine groups to react and crosslink two or more carbohydrate molecules. The amines may include aliphatic, cycloaliphatic and aromatic amines. They may be linear or branched, and have additional functionalities and linkages such as alcohols, thiols, esters, amides, acids, and ethers, among others. Exemplary amines may include 1,2-diethylamine, 1,3-propanediamine, 1,4-butanediamine, 1,5-pentanediamine, 1,6-hexanediamine, diaminoxylene, diethylenetriamine, triethylenetetramine, tetraethylenepentamine, as well as combinations of two or more of these amines. Natural and synthetic amino acids such as lysine, anginine, hestidine, etc., may also be used.

The curable amino-amide is formed through the selection of an unsaturated or saturated reactant that is an anhydride, carboxylic acid, ester, and salts and mixtures of such reactants. These unsaturated reactants may include maleic acid, fumaric acid, maleic anhydride, mono- and di-esters of maleic acid and fumaric acid, and salts and mixtures of these. Ammonium salts of the unsaturated acids of their monoesters conveniently can be utilized. Saturated reactants may include, without limitation, succinic anhydride, succinic acid, mono and diesters of succinic acid, glutaric acid and anhydride, phthalic acid and anhydride, tetrahydro phthaic acid and anhydride, mono and diesters of acid anhydrides and salts of the acids, and their mono esters.

In some formulations, the amino-amide product may be oligomerized before reacting with the carbohydrate. This oligomerization may be facilitated by heating the amino-amide solution until the amino-amide is dimerized, trimerized, tetramerized, etc., into the amino-amide oligomer. The heating conditions may include raising the temperature of the amino-amide solution to, for example, 120° C. to 150° C. for a time of up to 5 hours. In some instances, the oligomerized amino-amide product forms a stronger, more rigid cured binder product than then amino-amide monomer.

Then during the binder curing step, the majority of the carbohydrate reacts with the amino-amide intermediate, which contains an amic acid functional group, (i.e., an amide linkage in the vicinity of a carboxylic acid). An amic acid functional group is typically more reactive than a simple carboxylic acid. The amount of carbohydrate added is generally such that the molar ratio of carboxylic acid in the amino-amide to carbonyl or ketone in the carbohydrate is from 1:5 to 50:1, for example a ratio of 1:20 to 20:1, or a ratio of 1:10 to 10:1. Additional details about carbohydrate/amino-amide binder formulation are described in co-assigned U.S. patent application Ser. No. 12/539,263 to Shooshtari et al, filed Aug. 11, 2009, and titled "Curable Fiberglass Binder," the entire contents of which are herein incorporated by reference for all purposes.

2. Carbohydrate/Urea Derivative Binder Formulations

As discussed herein, the nitrogen-containing compound may include urea derivative reaction products of urea and/or substituted urea.

3. Carbohydrate/Nitrogen-Containing Salt Binder Formulations i. Salts of Inorganic Acids with Amines In additional carbohydrate binder formulations, the nitrogen-containing compounds may include a nitrogen-containing salt. For example, the nitrogen-containing compound may include the salt product of the combination of an inorganic acid and an amine (e.g., an amine-acid salt). Exemplary inorganic acids may include a phosphorous-containing acid such as phosphoric acid, pyrophosphoric acid, phosphorous acid, and phosphine, among others. Exemplary inorganic acids may also include oxygenated inorganic acids such as sulfuric acid, sulfurous acid, nitric acid, boric acid, hypochloric acid, chlorate acid, among others. They may also include non-oxygenated inorganic acids such as hydrochloric acid and hydrogen sulfide, among others.

Exemplary amines may include polyamines (e.g., diamines, triamines, etc.) having at least one primary amine group. For example, the amines may include ethylene diamine, 1,3-propanediamine, 1,4-butanediamine, 1,5-pentanediamine, 1,6-hexanediamine, α,α'-diaminoxylene, diethylenetriamine, triethylenetetramine, tetraethylenepentamine, as well as combinations of two or more of these amines.

When the amine-acid salt reacts with the carbohydrate under binder curing conditions the binder is formed. Exemplary binder systems include the combination of an amine-acid salt of 1,6-hexanediamine and phosphoric acid with the carbohydrate dextrose (HPD), the combination of an amine-acid salt formed from the combination of ethylene diamine and phosphoric acid with dextrose (EPD). Additional details about these amine-acid salt and carbohydrate binder formulations are described in co-assigned U.S. patent application Ser. No. 12/539,211, filed Aug. 11, 2009 to Shooshtari, the entire contents of which are herein incorporated by reference for all purposes.

ii. Salts of Inorganic Acids with Amines and Organic Species

Some carbohydrate/amine-acid salt binder formulations further include some combination of an organic acid, organic anhydride, and/or an alkanol amine. Exemplary organic acids may include polycarboxylic acid such as citric acid and or maleic acid. Exemplary organic anhydrides may include maleic anhydride, phthalic anhydride, methylphthalic anhydride, glutaric anhydride, tetrahydrophthalic anhydride, perhydrophthalic anhydride, itaconic anhydride, succinic anhydride, and trimellitic anhydride, among other anhydrides.

Exemplary alkanol amines may have the formula:

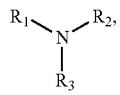

where $R_1$, $R_2$, and $R_3$ are independently chosen from, a hydrogen, a $C_{1-10}$ alkyl group, an aromatic group, and a $C_{1-10}$ hydroxy alkyl group, and wherein at least one of $R_1$, $R_2$, and $R_3$ is a hydroxyl alkyl group.

Specific examples of alkanol amines may include methanol amines such as mono-, di-, and tri-, methanol amine; ethanol amines such as monoethanol amine (MEA), diethanol amine (DEA), and triethanol amine (TEA); isopropanol amines such as mono-, di-, and tri-, isopropanol amine; methyldiethanol amine; ethyldiethanol amine; propyldiethanol amine; isopropyldiethanol amine; and n-butyldiethanol amine, among others.

Exemplary carbohydrate binder formulations may include the combination of a carbohydrate, amine-acid salt, and organic acid. These include binder formulations of dextrose, ethylene diamine phosphate, and citric or maleic acid. Additional details about these carbohydrate/amine-acid salt/organic acid binder formulations are described in co-assigned U.S. patent application Ser. No. 13/478,765, filed May 23, 2012 to Shooshtari et al., the entire contents of which are herein incorporated by reference for all purposes.

Exemplary carbohydrate binder formulations may also include the combination of a carbohydrate, amine-acid salt, organic anhydride, and alkanol amine. This include binder formulations of the reaction products of monoethanol amine ("E") and maleic anhydride ("M") combined with ethylenediamine phosphate ("EP") and dextrose ("D") to make binder compositions referred to as EMEPDs. In still other exemplary binder formulations, the amine-acid salt may be eliminated. This includes formulations of the reaction products of monoethanol amine ("E") and maleic anhydride ("M") with the carbohydrate dextrose to make binder compositions referred to as EMDs. Additional details about these carbohydrate/amine-acid salt/anhydride-alkanol amine binder formulations are described in co-assigned U.S. patent application Ser. No. 13/559,769, filed Jul. 27, 2012 to Shooshtari et al., the entire contents of which are herein incorporated by reference for all purposes.

Exemplary binder formulations may include additional compounds combined with the reducing sugar, organic acid, and amine salt of an inorganic acid. For example, urea may also be included with the other binder components. Exemplary, urea-containing binder compositions may include ethylene diamine phosphate ("EP"), citric acid ("C"), urea ("U"), and dextrose ("D") combined to make a binder composition referred to as EPCUD. Exemplary molar ratios of these components may include Ethylenediamine:Phosphoric Acid:Citric Acid:Urea:Dextrose of 1:1:0.5:1:6.

iii. Ammonium Salts of Carboxylic Acids

In still additional carbohydrate binder formulations, the nitrogen-containing compounds may include an ammonium salt of a polycarboxylic acid. Exemplary ammonium salts of polycarboxylic acids may be formed from the reaction of ammonia ($NH_3$) with the polycarboxylic acid to form the ammonium salt. It should be appreciated that other types of ammonium ions can function as the cation in the ammonium-polycarboxylate salt, such as $(NH_3R_1)^+$, $(NH_2R_1R_2)^+$, and $(NHR_1R_2R_3)^+$, where $R_1$, $R_2$, and $R_3$ are each independently chosen from an alkyl, cycloalkyl, alkenyl, cycloalkenyl, heterocyclyl, aryl, and heteroaryl, among other organic groups.

Exemplary polycarboxylic acids may include dicarboxylic acids, tricarboxylic acids, etc. Dicarboxylic acids may include maleic acid, and tricarboxylic acids may include citric acid.

The binder formulations may include the combination of a carbohydrate (e.g., a reducing sugar) with the ammonium salt of the polycarboxylic acid. For example, the binder composition may include dextrose and triammonium citrate.

4. Carbohydrate Blends with Latex and/or Solution Polymers

This group of carbohydrate binder compositions is distinguished by the inclusion of the components of a second binder in the formulation. The second binder may be a latex binder and/or solution polymer with a significantly higher viscosity than the carbohydrate binder composition. In some instances, the second binder may act as the sole thickening agent in the carbohydrate binder composition, while in other instances the second binder may complement other thickening agents to get the composition to a target viscosity.

The second binder may include latex binders having a Brookfield viscosity of about 100 cPs or more (spindle 18 operating at a speed of 60 rpm) at 20° C. Exemplary second binders may include acrylic binders, among others. The second binder may be present up to about half the weight of the total binder composition (e.g., 1 to 50 wt. %; 1 to 20 wt. %; etc.).

5. Additional Binder Components

The present carbohydrate binder compositions may further include one or more additional components such as adhesion prompters, oxygen scavengers, solvents, emulsifiers, pigments, organic and/or inorganic fillers, flame retardants, anti-migration aids, coalescent aids, curing catalysts, wetting agents, biocides, plasticizers, organosilanes, anti-foaming agents, colorants, waxes, suspending agents, anti-oxidants, and secondary crosslinkers, among other components. In some instances, some or all of the additional components are pre-mixed with the binder composition before it is applied to fibers and cured. In additional instances, some or all of the additional components may be introduced to the curable, curing, and/or cured fiber-containing composite during or after the initial binder composition is applied to the fibers.

EXAMPLES

Example 1A

Tensile Strength Testing of Dextrose Binder Composites

Comparative tensile strength tests were conducted on composites made with an exemplary dextrose/urea-glyoxal binder composition and composites made with a standard commercial polyacrylic binder composition. The dextrose/urea-glyoxal composition was prepared by mixing 60 g of urea, 145 g of a 40 wt % solution of glyoxal, at a temperature of 90° C. for about 120 minutes. The urea and glyoxal react to form crosslinking agents for the binder composition, including cyclic urea-glyoxal compounds (e.g., 4,5-dihydoxyimidazolidin-2-one). Next, 918 g of water and 989 g of dextrose monohydrate (900 g active) were added to the reacted urea-glyoxal solution to form the uncured binder composition for making the dogbone composite. To this solution was added 76.4 g ammonium sulfate as a catalyst. The uncured polyacrylic binder composition was made by mixing a commercial polyacrylic acid (QRXP-1765 acrylic resin from Dow Chemical) with triethanol amine that acted as a crosslinking agent.

Each of the binder compositions was formulated into 25 g samples having a 50 wt. % solids level and mixed with 1000 g of glass beads to make uncured composites. Roughly 1 ounce samples of the uncured composites were then spread into dogbone molds and pressed in the molds at a pressure of about 10,000 lbs. The dogbone samples were then released from the molds and heated at about 400° F. for about 20 minutes to form cured dogbone composites. The cured dogbone composites were roughly 25 mm wide and 6 mm thick.

Figure 5:
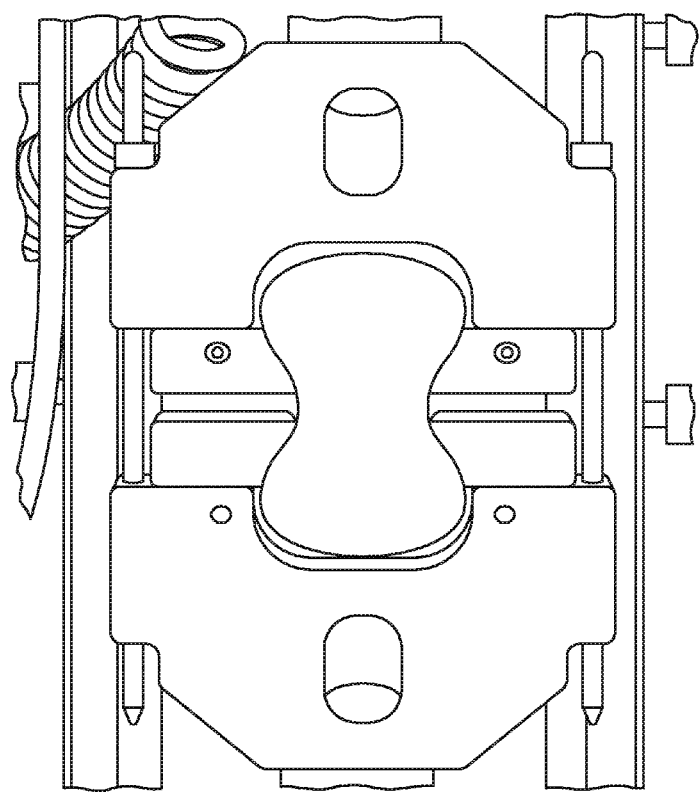
FIG. 5 is a picture of a cured dogbone composite placed in an Instron tensile strength measuring instrument.

The cured dogbone composites were tested for tensile strength in both an unaged condition and after being aged in a high humidity atmosphere. The unaged composites were taken directly from the curing oven and placed in an Instron tensile strength testing instrument (Harry W. Dietert Co.—Tensile Core Grip Assembly Part No. 610-7CA) as shown in FIG. 5. The aged composites were taken from the curing oven and placed for 24 hours in a humidifying oven set at approximately 95% humidity and 120° F. After the aged samples were cooled for approximately 8 hours, they were placed in the Instron instrument to test their tensile strength.

Figure 6:
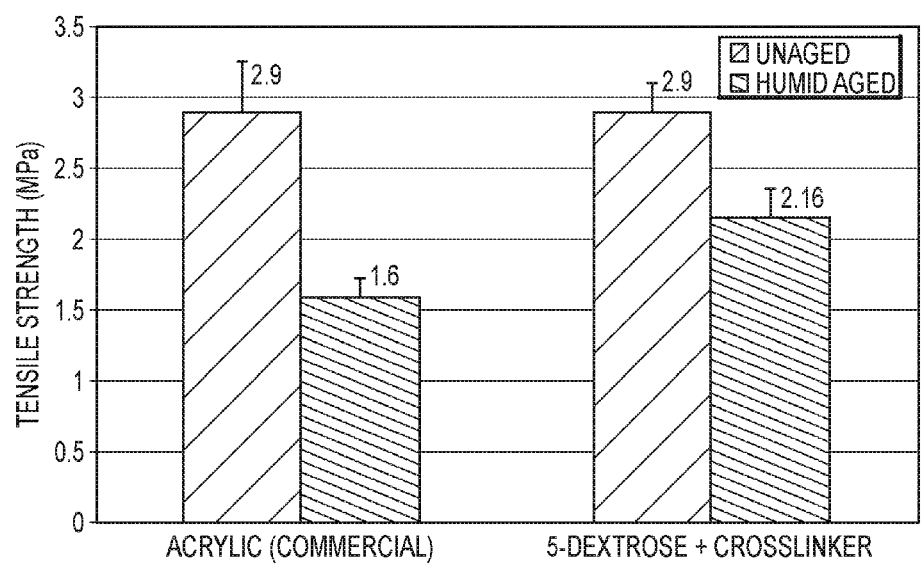
FIG. 6 is a graph with dogbone tensile strength test results for binder composites according to embodiments.

FIG. 6 is a graph showing the dogbone tensile strength test results for the dextrose/urea-glyoxal binder under unaged and humid-aged conditions, as well the strength test results for the comparative composite made from the commercial polyacrylic acid binder. The results demonstrate that the unaged dextrose/urea-glyoxal binder and an almost identical tensile strength as the unaged commercial polyacrylic binder at 2.9 MPa. When both samples were aged at 120° F. and 95% humidity for 24 hours, the aged dextrose/urea-glyoxal binder showed significantly higher tensile strength (2.15 MPa) compared with the aged polyacrylic binder (1.6 MPa).

Example 1B

Tensile Strength Testing of Fructose/Dextrose Binder Composites

Additional tensile strength tests were conducted on composites made with exemplary binder compositions that included combinations of fructose and dextrose reacted with a urea-glyoxal crosslinking agent. A first fructose+dextrose/urea-glyoxal binder composition was prepared by mixing 60 g of urea, 145 g of a 40 wt % solution of glyoxal, at a temperature of 90° C. for about 120 minutes. The urea and glyoxal react to form crosslinking agents for the binder composition, including cyclic urea-glyoxal compounds (e.g., 4,5-dihydoxyimidazolidin-2-one). Next, 918 g of water and 989 g of 42 wt. % fructose and 55 wt. % dextrose monohydrate were added to the reacted urea-glyoxal solution to form the uncured binder composition for making the dogbone composite. To this solution was added 76.4 g ammonium sulfate as a catalyst. A second fructose+dextrose/urea-glyoxal binder composition was prepared using the same components and preparation method, except the fructose:dextrose ratio was changed to 55 wt. % fructose and 42 wt. % dextrose. Dogbone composites were prepared from both the first and second fructose+dextrose/urea-glyoxal binder compositions in the same method as described in Example 1A above. The dogbone tensile strength test results demonstrated similar tensile strengths for the fructose+dextrose/urea-glyoxal binder compositions as the dextrose-only compositions.

Example 2

Preparation of an Exemplary Glass-Fiber Composites

A glass-fiber composite was made from a dextrose/urea-glyoxal binder composition and a nonwoven glass fiber mat. Preparation of the binder composition started by mixing 60 kg or urea into a 145 kg aqueous glyoxal solution (40 wt. % glyoxal (58 kg on dry basis)) at room temperature until the urea dissolved. The urea-glyoxal solution temperature was then increased to 80° C. and kept at 80-85° C. for 2 hours while stirring the solution at 500 rpm to facilitate the reaction of the urea and glyoxal. At the end of the reaction period, a 57 wt. % solution of the urea-glyoxal crosslinking agent was formed.

918 kg or water and 989 kg of dextrose monohydrate (900 kg active) were added to the crosslinking solution and the combined mixture was stirred until the dextrose dissolved. The mole ratio of urea:glyoxal:dextrose in the solution was 1:1:5. 76.4 kg of ammounium sulfate was added to the solution as a catalyst, and stirred until the catalyst dissolved to make the binder composition.

Manufacture and Testing of R19 Fiberglass Insulation Batts

The binder composition was spray coated onto a nonwoven glass-fiber mat made from blown filaments of sodium borosilicate glass having diameters ranging from about 1 to 10 μm and lengths ranging from of about 5 to 100 mm. The amalgam of the fibers and binder composition was then conveyed through a curing oven operated at a temperature of 150° C. to 350° C. to heat the amalgam to a curing temperature for about 30 seconds to 3 minutes. The bat of glass fibers held together by the cured binder emerged from the oven with an approximate thickness of about 3 to 4 cm and a nominal weight of about 440 g/m$^2$ and density of about 11.2 kg/m$^3$.

The cured bat was used to make R-19 building insulation. The droop (rigidity) and recovery of the batts were evaluated under unaged conditions, as well as after aging for 7 and 14 days at 120° F. and 95% humidity. The performance of the batts made with the dextrose-urea-glyoxal binder composition was compared to bats made with conventional binder compositions. The comparative tests found the unaged batts made with the dextrose-urea-glyoxal binder composition had 10% improved rigidity (i.e., lower sag) compared with comparable batts made with a conventional binder composition (acrylic), and the aged batts showed an even larger 20% improvement in rigidity (lower sag). This improvement in the rigidity of the batts made with the dextrose-urea-glyoxal binder composition did not result in any diminishment of their recovery performance compared to the conventional batts. In addition, the emissions of volatile organic compounds (VOCs) from batts made with the urea/glyoxal/dextrose binder compositions were significantly lower than batts made with the conventional acrylic binder compositions. No release of formaldehyde was detected from the urea/glyoxal/dextrose batts. Table 1 below summarizes the droop, recovery, and VOC emissions results for the various sample batts tested:

TABLE 1

Droop and Recovery Results for R19 Insulation Batts

| Sample | Droop (Rigidity) – [Inches] | Recovery – [Inches] | VOC Emissions – [lb/hour] |
|---|---|---|---|
| Urea/glyoxal/dextrose binder composition (unaged) | 2.1 | 6.7 | 0.8 |
| Urea/glyoxal/dextrose binder composition (Aged 7 days) | 3.4 | 6.0 | N/A |
| Urea/glyoxal/dextrose binder composition (Aged 14 days) | 3.5 | 6.0 | N/A |
| PF Binder (unaged) | 2.5 | 6.5 | 0.9 |
| PF Binder (Aged 7 days) | 4.2 | 6.1 | N/A |
| PF Binder (Aged 14 days) | 4.5 | 6.0 | N/A |

Manufacture and Testing of Duct Board

The present dextrose-urea-glyoxal binder compositions are also used to make duct board. Two compositions were independently prepared using 145 kg of 40 wt. % aqueous glyoxal mixed with 60 kg urea and 989 kg dextrose monohydrate. 76.4 kg of ammonium sulfate was added to one of the compositions, while 50 kg of ammonium sulfate and 50 kg of diammonium phosphate was added to the other. Each of the binder compositions was used to make 1.9 cm thick duct board having a binder content of 18 wt % and density of 700 kg/m$^3$ using standard process conditions (e.g., cure temperature of 500-550° F.).

The structural characteristics and volatile organic compound (VOC) emissions of the duct boards were tested and compared to duct board made with a conventional phenol-formaldehyde (PF) binder composition. The results showed that the droop (rigidity) and El modulus of the duct boards made with the urea/glyoxal/dextrose binder compositions improved by about 20% compared to the duct boards made with the conventional PF binder composition. The present duct boards also had significantly reduced VOC emissions compared to the PF board. The improvements in the duct boards' structural characteristics were similar for the urea/glyoxal/dextrose binder compositions that included ammonium sulfate [(NH$_4$)$_2$SO$_4$] alone versus the combination of ammonium sulfate and diammonium phosphate [(NH$_4$)$_2$SO$_4$ and (NH$_4$)$_2$HPO$_4$]. Table 2 below summarizes the droop, El modulus, and VOC emisons results for the various duct boards tested:

TABLE 2

Droop and El Modulus Results for Duct Boards

| Sample | Droop (Rigidity) – [Inches] | El Modulus – [N · m$^2$?] |
|---|---|---|
| Urea/glyoxal/dextrose binder composition with (NH$_4$)$_2$SO$_4$ alone | 2.5 | 183 |
| Urea/glyoxal/dextrose binder composition with (NH$_4$)$_2$SO$_4$ and (NH$_4$)$_2$HPO$_4$ | 1.3 | 153 |
| Conventional Phenol-Formaldehyde binder Composition | 2.5 | 145 |

Additional Characteristics of the Present Insulation Batts and Duct Boards

Fiberglass insulation batts and duct boards made with the present urea/glyoxal/dextrose binder compositions were measured on a number of characteristics described in Table 3 below. For all the characteristics, the batts and boards met or exceeded current standards requirements for residential and commercial building materials set by the American Society for Testing and Materials (ASTM) and Underwriters Laboratory (UL).

TABLE 3

Characteristics of R19 Insulation Batt and Duct Boards

| Characteristic | R19 Insulation Batt | Duct Board |
|---|---|---|
| Density | 0.25-0.75 lbs/ft$^3$ | 2.0-6.0 lbs/ft$^3$ |
| Loss on Ignition (LOI) | 3 wt. %-6 wt. % | 15 wt. %-22 wt. % |
| Tensile Strength | 0.35-1.0 psi | |
| Thickness Recovery | 5 inches-7 inches | 0.9 inches-1.1 inches |
| Dust Testing | 10-50 g/10,000 ft$^2$ | 0.03-0.3 g/lb |
| Water Absorption | >0.5 wt % | >5 wt. % |
| Flexural Rigidity (E · I) | | <400 EI |
| Stiffness-Rigidity | ≤5 inches for 36 inch span | |
| Hot Surface Performance | | Meets C411 Requirements |
| Corrosivity on Steel | Mass loss corrosion rate <5 ppm chloride reference solution (ASTM C1617) | Mass loss corrosion rate <5 ppm chloride reference solution (ASTM C1617) |
| Smoke Development on Ignition | Flame spread of <25, and smoke developed <50 using ASTM E84; Classified as Non-Combustible based on ASTM E136. | Flame spread of <25, and smoke developed <50 using ASTM E84 |

Example 3

Varying the Mole Ratio of Urea and Glyoxal in Binder Composition

In this example, the properties of binder compositions were compared that used urea/glyoxal reaction products with different starting mole ratios of urea and glyoxal. Three samples were prepared where the mole ratio of urea-to-glyoxal was 2:1, 1:1, and 1:2. Each of the urea/glyoxal reaction products were made by combining the urea and glyoxal reactants at the respective mole ratios into a 50 wt % aqueous solution
Formation of Urea:Glyoxal 1:2/Dextrose Binder:

To 290 g of a 40% solution of glyoxal (116 g active) in a three neck round bottom flask equipped with stirrer, condenser and temperature control added 60 g urea (1 mole) at ambient temperature. After all urea dissolved, the temperature was increased to 90° C. and kept for 60 min until all reactants were consumed and (2R,3S,6R)-2,3,5,6-tetrahydroxy-1,4-diazabicyclo[2.2.1]heptan-7-one product was formed as determined by HPLC. This solution was added to a 50% solution of six moles of dextrose (1080 g) in water at 60° C. After the two solutions mixed, enough water was added to bring the final concentration to 50%.

Formation of Urea:Glyoxal 2:1 (Glycoluril)/Dextrose Binder:

To 145 g of a 40% solution of glyoxal (58 g active) in a three neck round bottom flask equipped with stirrer, condenser and temperature control added 120 g urea (2 moles) at ambient temperature. After all urea dissolved, the temperature was increased to 90° C. and kept for 120 min until all reactants were consumed and glycoluril product was formed as determined by HPLC. This solution was added to a 50% solution of six moles of dextrose (1080 g) in water at 60° C. After the two solutions mixed, enough water was added to bring the final concentration to 50%.

As noted above, the predominant reaction product of the urea and glyoxal depend on the mole ratio of the two reactants. Table 4 lists the predominant reaction product for each of the three samples:

TABLE 4

Predominant Urea/Glyoxal Reaction Products for Different U:G Mole Ratios

| Urea:Gloyxal Mole Ratio | Predominant Reaction Product |
|---|---|
| 2:1 | 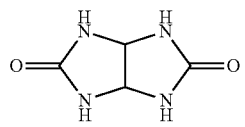 tetrahydroimidazo[4,5-d]imidazole-2,5(1H,3H)-dione |
| 1:1 | 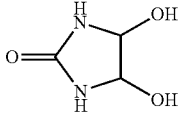 4,5-dihydroxyimidazolidin-2-one |
| 1:2 | 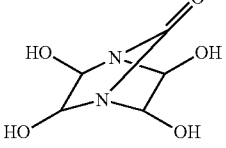 (2R,3S,6R)-2,3,5,6-tetrahydroxy-1,4-diazabicyclo[2.2.1]heptan-7-one |

One mole of each urea-glyoxal reaction product was added to six moles of an aqueous dextrose solution to make three 50 wt. % solutions. An ammonium sulfate/ammonium phosphate catalyst was then added to each of the solutions to make three sample binder compositions. The catalyst was a 1:1 mixture of ammonium sulfate:diammonium phosphate dissolved in water to make a 40% active solution. Catalyst was added at 10% active ingredient based on solid resin.

Each of the three sample binder compositions was formulated into 25 g samples having a 50 wt. % solids level and mixed with 1000 g of glass beads to make uncured composites. Roughly 1 ounce samples of the uncured composites were then spread into dogbone molds and pressed in the molds at a pressure of about 10,000 lbs. The dogbone samples were then released from the molds and heated at about 400° F. for about 20 minutes to form cured dogbone composites. The cured dogbone composites were roughly 25 mm wide and 6 mm thick.

Figure 7:
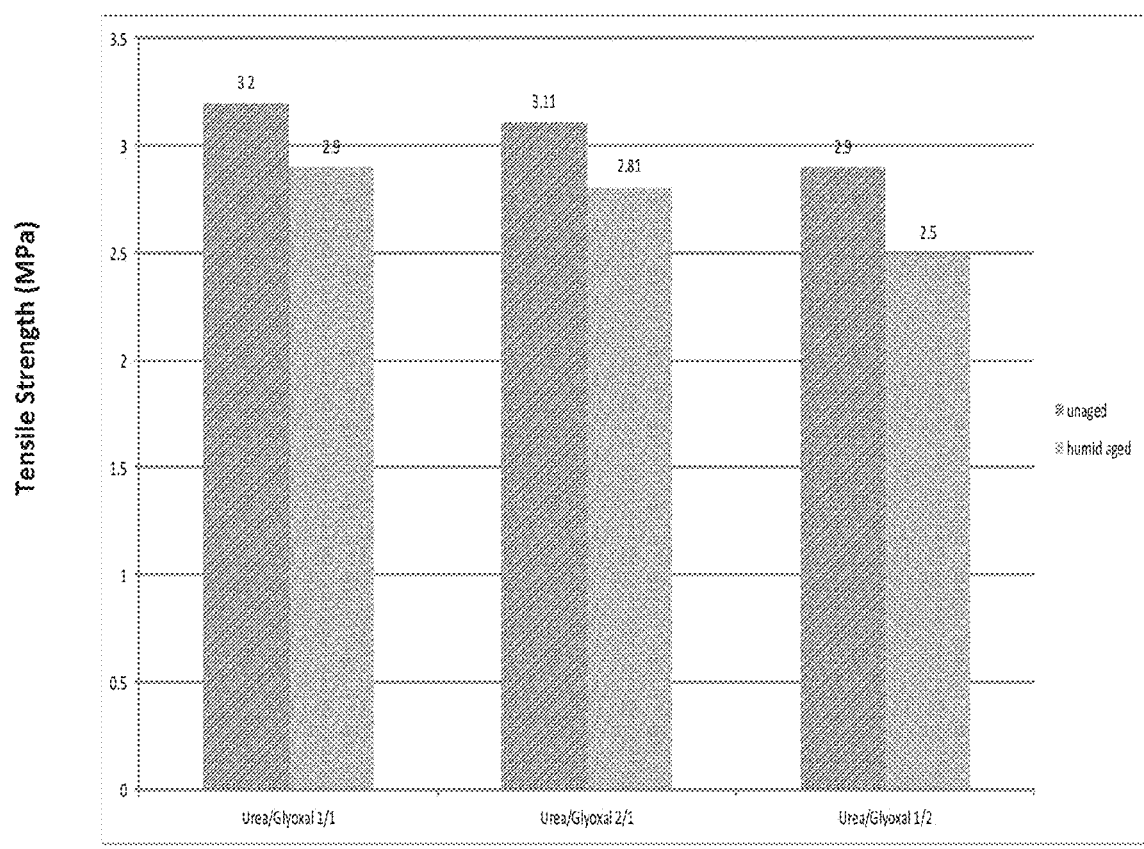
FIG. 7 is a graph with dogbone tensile strength test results for binder composites according to embodiments.

The cured dogbone composites were tested for tensile strength in both an unaged condition and after being aged in a high humidity atmosphere in the same manner described in Example 1A above. FIG. 7 is a graph showing the dogbone tensile strength test results for the dextrose/urea-glyoxal binder compositions under unaged and humid-aged conditions. The results show that binder compositions using urea-to-glyoxal mole ratios of 1:1 and 2:1 have similar unaged tensile strength results at about 3.2 MPa, and similar aged tensile strength results at 2.9 MPa. The binder composition with the 1:2 mole ratio had about 10% lower unaged tensile strength at 2.9 MPa, and a similar reduction for aged tensile strength at 2.5 MPa.

It was further observed that the binder composition with the 1:2 mole ratio of urea-to-glyoxal was the softest of the three samples, and did not crack or break when used as a 15 wt. % binder in a glass mat reinforced composition sheet that was bent around a 5 mm diameter pipe. Thus, exemplary binder compositions that use the 1:2 mole ratio of urea-to-glyoxal may be particularly well suited for pipe insulation and other articles that require significant wrapping and/or bending of the insulation material.

Example 4

Exemplary Binder Compositions Using Crosslinking Agents Other than Urea-Glyoxal

Three binder compositions were made that included the reaction products of urea and a dial or diol, which functioned as a crosslinking agent in the compositions. The urea was provided in aqueous solutions prepared by dissolving 1 mole (60 g) of urea to a 50% solids solution in room temperature water. The aqueous urea solutions were prepared in a three-neck flask equipped with a stirrer and a condenser. One of the urea solutions was combined in the flask with 1 mole of 1,3 propane dial (72 g), while a second urea solution was combined in the flask with 1 mole of 2,4 pendate dione (99 g), and a third urea solution was combined in the flask with 2,3 butane dione (86 g). Each combination of urea and dial or diol was refluxed for 120 minutes to form the reaction product.

Figure 8:
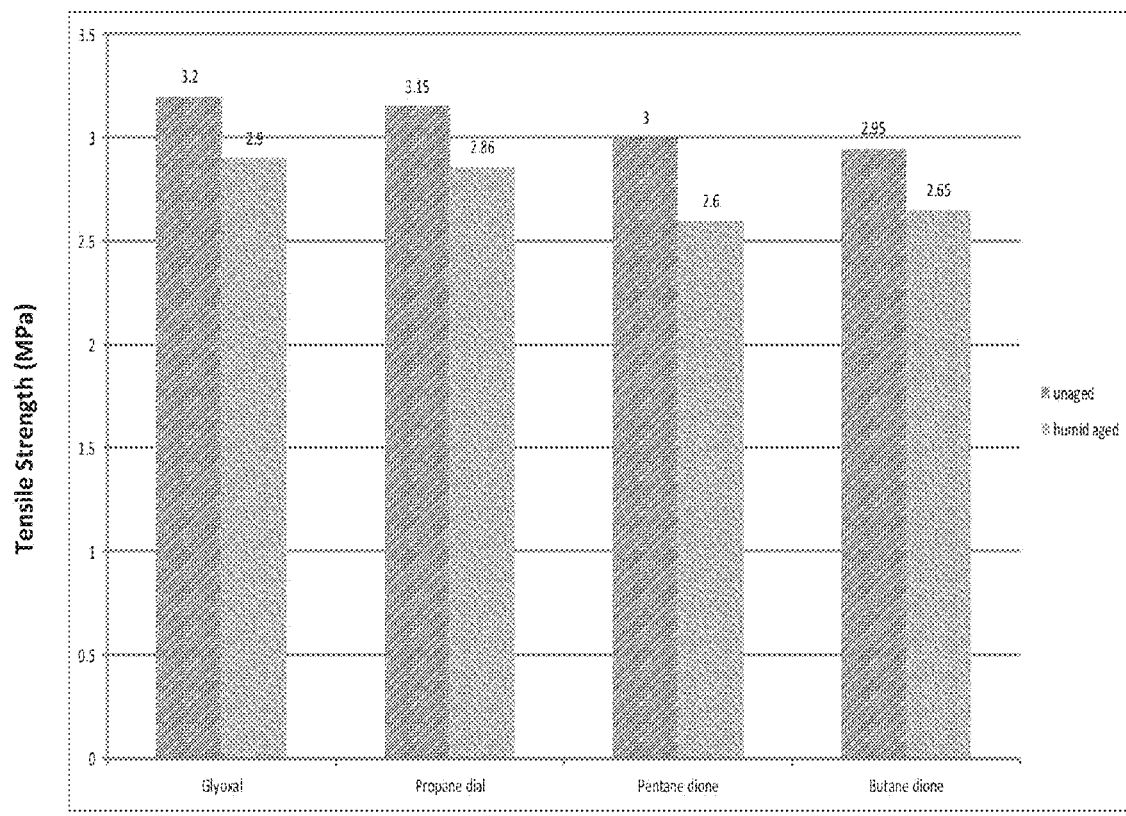
FIG. 8 is a graph with dogbone tensile strength test results for binder composites according to embodiments.

One mole of each of the three crosslinking agent solutions was added to 6 moles (1080 g) of a 50% solids aqueous dextrose solution (i.e., 1080 g of dextrose dissolved in 1080 g or water). After addition of crosslinking agent solutions to each of the dextrose solutions, the temperature of the combined solutions was increased to 90° C. for 15 minutes followed by a rapid cooling to ambient temperature. Dogbone composite were prepared as explained previously and the results are shown in FIG. 8.

Figure 9:
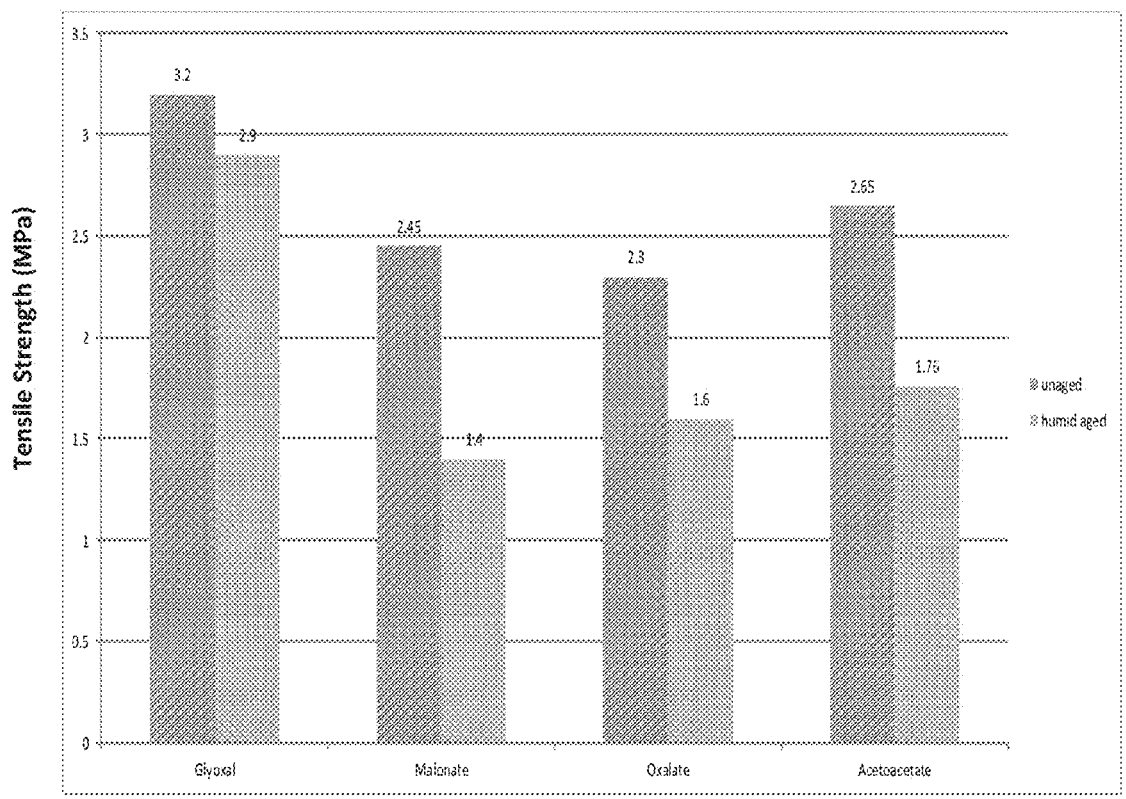
FIG. 9 is a graph with dogbone tensile strength test results for binder composites according to embodiments.

In another set of experiments, one mole of urea (60 g) was dissolved in 200 g of methanol. To such solution one mole of the following was added: dimethyl malonate (132 g), dimethyl oxalate (118 g) and methyl acetoacetate (116 g). To these solutions added 0.54 g sodium methoxide (0.01 mole) and the solutions were brought to a reflux for 120 minutes. The methoxide was neutralized by addition of acetic acid. After evaporation of methanol in a rotavap, the white powder crosslinking agents were added to a solution of six moles of dextrose (1080 g) in enough water at 60° C. to make a final 50% solid solutions. The solutions were briefly heated to 90° C. for 15 minutes and cooled to ambient temperature rapidly. Dogbone composite data is shown for these binders in FIG. 9.

Example 5

Tensile Strength

Figure 10:
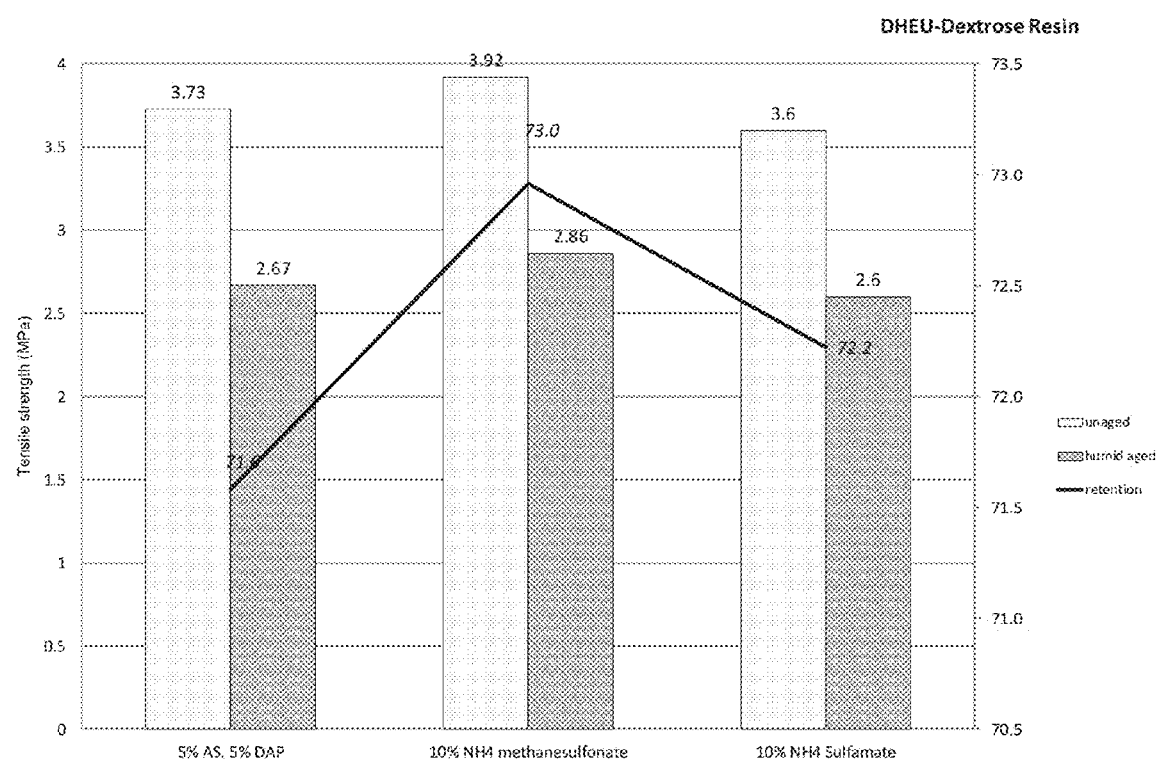
FIG. 10 is a graph with dogbone tensile strength test results for binder composites according to embodiments.

FIG. 10 shows dogbone composite data for dihydroxyethylene urea (DHEU)-dextrose binder using three catalysts: 5% ammonium sulfate/5% diammonium phosphate; 10% ammonium methane sulfonate; and 10% ammonium sulfamate. Tensile strength is shown for unaged and humid aged samples. The results show equal or better mechanical performance with ammonium methane sulfonate and ammonium sulfamate as with the ammonium sulfate/diammonium phosphate catalyst. The sulfonate and sulfamate samples retain mechanical strength at a higher percentage than the sulfate/phosphate sample.

Example 6

Cure Kinetics

Figure 11:
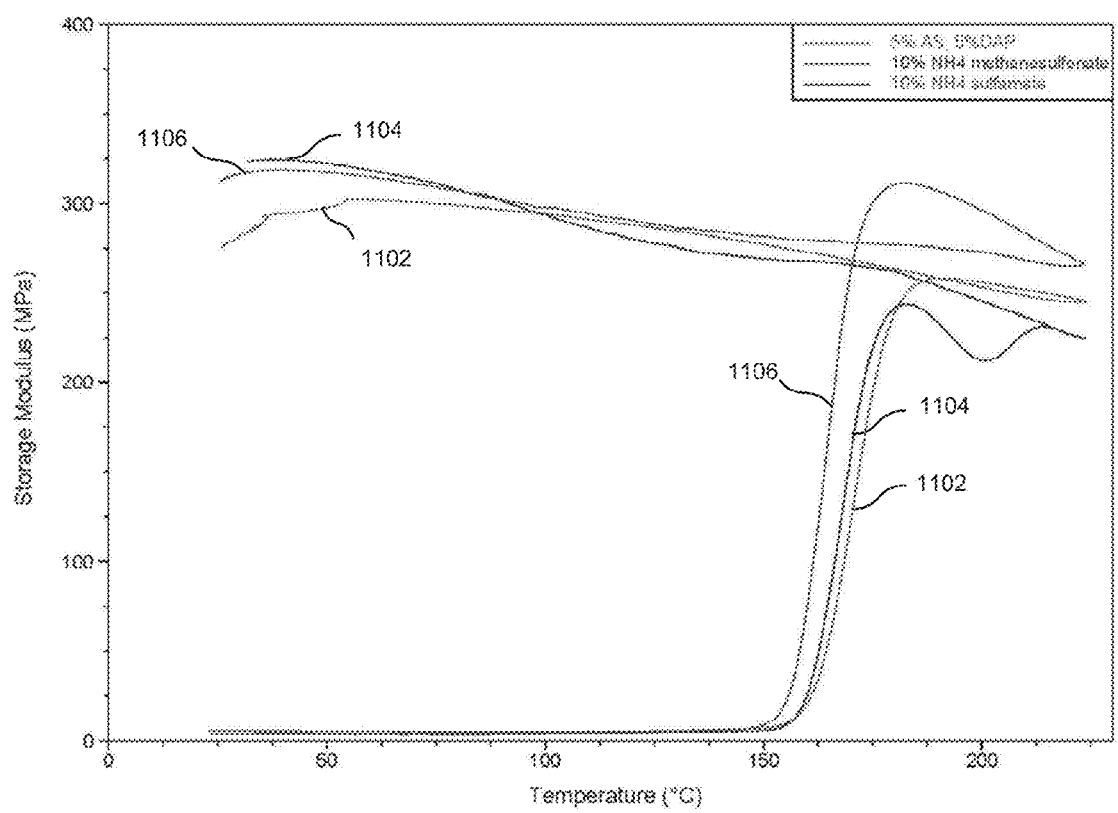
FIG. 11 shows cure kinetics for binders with different catalysts according to embodiments of the present technology.

FIG. 11 shows Dynamic Mechanical Analyzer (DMA) results for the catalysts. Binder compositions with the sulfamate and sulfonate catalysts show faster cure kinetics than a sulfate/phosphate catalyst. FIG. 11 shows modulus (force) as a function of temperature. Line 1102 shows results for a 5% ammonium sulfate/5% diammonium phosphate catalyst. Line 1104 shows results for a 10% ammonium methane sulfonate catalyst. Line 1106 shows results for a 10% ammonium sulfamate catalyst. The temperature at which the storage modulus increases is the measured onset of cure. The sulfonate and sulfamate catalysts are observed to have a lower cure temperature than the sulfate/phosphate catalyst.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the fiber" includes reference to one or more fibers and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A carbohydrate binder composition comprising:
   dextrose,
   4,5-dihydroxyimidazolidin-2-one, and
   a catalyst that catalyzes a reaction between the dextrose and 4,5-dihydroxyimidazolidin-2-one, the catalyst comprising a salt of an oxyacid, wherein the oxyacid is selected from the group consisting of a methyl sulfamic acid, an ethyl sulfamic acid, a propyl sulfamic acid, and a butyl sulfamic acid.

2. The carbohydrate binder composition of claim 1, wherein the salt comprises a reaction product of the oxyacid with a compound selected from the group consisting of an ammonia, an alkyl amine, an aryl amine, an alkanol amine, a diamine, and a polyamine.

3. The carbohydrate binder composition of claim 1, wherein the salt comprises a reaction product of the oxyacid with an amine selected from the group consisting of a methyl amine, an ethyl amine, a dimethyl amine, and a trimethyl amine.

4. The carbohydrate binder composition of claim 1, wherein the salt comprises a reaction product of the oxyacid with an alkanol amine selected from the group consisting of a monoethanol amine, a diethanol amine, and a triethanol amine.

5. The carbohydrate binder composition of claim 1, wherein the catalyst is a first catalyst, and
   the carbohydrate binder composition further comprises an additional catalyst or additional catalysts, wherein:
      the additional catalyst or additional catalysts comprise a sulfate, a nitrate, or a phosphate, and
      the additional catalyst or additional catalysts have a total weight no more than one-ninth of the weight of the first catalyst on a dry basis.

* * * * *